United States Patent [19]

Light et al.

[11] Patent Number: 4,899,590
[45] Date of Patent: Feb. 13, 1990

[54] PUMP SHAFT INSPECTION SYSTEM

[75] Inventors: Glenn M. Light; Edward A. Bloom, both of San Antonio, Tex.; Soung-Nan Liu, Freemont, Calif.

[73] Assignee: Electric Power Research Institute, Palo Alto, Calif.

[21] Appl. No.: 271,940

[22] Filed: Nov. 15, 1988

[51] Int. Cl.[4] .................................................. G01N 29/04
[52] U.S. Cl. ........................................................... 73/622
[58] Field of Search ....................... 376/245, 249, 252; 73/622, 625, 628

[56] References Cited

U.S. PATENT DOCUMENTS

| | | | |
|---|---|---|---|
| 3,636,778 | 1/1972 | Huffstetler | 73/622 |
| 3,960,006 | 6/1976 | Smith | 73/622 |
| 4,165,648 | 8/1979 | Pagano | 73/625 |
| 4,479,387 | 10/1984 | Wagner et al. | 73/622 |
| 4,660,419 | 4/1987 | Derkaes et al. | 73/622 |

Primary Examiner—Harvey E. Behrend
Assistant Examiner—Daniel Wasil
Attorney, Agent, or Firm—Leonard Bloom

[57] ABSTRACT

An inspection system for non-destructively detecting physical defects in solid shafts by launching and receiving longitudinal acoustic waves has been described incorporating a transducer head containing a transducer head containing a matrix of transducers, pulsers, pulse width modulators, preamplifiers and a summing amplifier. A fiber optic cable may couple the transducer head to a remote location containing a receiver and a oscilloscope. The invention overcomes the problem of launching longitudinal acoustic waves with insufficient energy. Further, the invention overcomes the problem of asymmetric load conversions affecting the output signal arising at times when only one transducer is used and is positioned off center with respect to the solid shaft.

2 Claims, 2 Drawing Sheets

PUMP SHAFT INSPECTION SYSTEM

BACKGROUND OF THE INVENTION

1. Field of the Invention

This invention relates to non-destructive evaluation of solid objects and more particularly, to ultrasonic wave inspection systems for the detection of cracks in solid objects.

1. Description of the Prior Art

Reactor coolant pumps are an integral part of the reactor cooling system. These pumps are responsible for pumping coolant into the core during the operation of a nuclear power plant. The failure of a reactor coolant pump would result in a decreased amount of coolant getting into the core and could cause exceedingly high temperatures to occur in the core. If more than one failed (which is highly improbable) or if the pump impeller were to break the integrity of the coolant system, then a major loss of coolant could occur. This could potentially lead to core overheating. Therefore, the failure of a reactor coolant pump is a major safety concern.

The reactor coolant pump is a high horsepower unit. The pump shaft, which is usually fabricated from heavy stainless steel, must transform the torque of the motor into pumping power and it is therefore subjected to very high stresses. Therefore, pump shafts are susceptible to fatigue cracking due to these large cyclic stresses. Since the shaft has so many diameter changes and usually has a threaded region, any defects in these regions can act as stress risers and ultimately to crack initiation sites.

In the history of these coolant pumps, no failures have been reported until 1985. At that time, the failure of a reactor coolant pump shaft at a nuclear power plant was reported. As a result of this failure, several utilities which had similar pumps were required to perform inspections on their pumps and provide data on the integrity of their pumps to the Nuclear Regulatory Commission. The results of these inspections showed several shafts with indications of cracking. However, after these pumps were disassembled and the pump shafts inspected with liquid penetrant, the cracks were not confirmed with the liquid penetrant. This led to the need for improving the reliability of ultrasonic inspection for the detection of cracks in the pump shaft.

A reactor coolant pump shaft is a long, large diameter, cylindrical body, which has many variations in diameter along its length. The pump shaft is directly mated to the pump impeller and sustains a great amount of stress from converting the torque of the high horse power motor into pumping force.

Pump shafts can be inspected in several ways which require various stages of pump disassembly. One way is to disassemble the pump so that the pump shaft is totally accessible. In this mode, liquid penetrant techniques can be used to detect cracking. However, disassembly of the pump is costly and very time consuming. Therefore, it is desirable to utilize non-destructive evaluation (NDE) techniques that can be used with the pump in situ and require minimal pump disassembly.

Ultrasonics is the most often used NDE method for inspecting pump shafts in situ. Two ultrasonic techniques have been used; namely, 0-degree longitudinal wave and the high angle longitudinal wave. Each technique requires different stages of pump disassembly.

When the 0-degree longitudinal wave technique is used, the cover of the pump must be removed which exposes the flat end of the pump shaft. To utilize the high angle longitudinal wave technique, further disassembly of the pump is required to remove seals so that almost the entire length of the pump shaft is exposed. To date, use of both of these techniques have lead to some inconclusive inspection results. In utilizing the conventional 0-degree longitudinal wave technique, a transducer with a frequency in the range of 1–2.25 MHz with a diameter of approximately 2.54 cm (1 inch) to 3.81 cm (1.5 inches) is used to scan over the surface of the exposed end of the pump shaft. The pump shaft may have a center hole which is not scanned over. There are two problems associated with this inspection. First, the small diameter transducer does not provide sufficient energy into the pump shaft. The energy input is related to the size of the transducer. Secondly, the small transducer produces mode-converted signals which can be difficult to interpret, especially since the transducer beam is striking the pump shaft wall asymmetrically.

When the high angle longitudinal wave technique is used, more pump disassembly is required so that the transducer beam can intersect the regions of interest. This technique has been susceptible to giving indications due to metallurgical variations in the pump shaft which are not detrimental to the pump shaft condition. Therefore, the high angle longitudinal wave technique requires too much pump disassembly and has been observed to give false indications due to metallurgical variations in the pump shaft.

SUMMARY OF THE INVENTION

In accordance with the present invention, an apparatus and method is provided for inspecting a solid shaft for physical defects comprising a matrix of transducers positioned within a predetermined range of one another to form a large transducer head having a large aperture for generating bulk longitudinal acoustic waves into a solid shaft into a substantial surface area of the shaft at an exposed end to provide longitudinal acoustic waves travelling in the direction of the longitudinal axis of the solid shaft, each transducer including piezoelectric crystal material, each transducer coupled to the output of a respective pulser for applying a voltage across the transducer for generating the bulk longitudinal acoustic waves, each transducer coupled to the input of a respective preamplifier for amplifying electrical signals generated across the transducer in response to the receipt of reflected ultrasonic wave energy, an output of each preamplifier coupled to a respective input to a summing amplifier to provide the algebraic sum of the input signals at an output of the summing amplifier, each pulser having an input coupled to the output of a respective pulse width modulator, each pulse width modulator having an input for receiving a trigger pulse and includes circuitry for generating a square wave of predetermined width with respect to its respective transducer it is driving to compensate for variations in transducer parameters.

It is an object of the invention to provide a transducer head for introducing more acoustic energy into the solid shaft to be inspected.

It is a further object of the invention to provide a transducer head which may be positioned to produce longitudinal acoustic waves coaxially with the longitudinal axis of the solid shaft from one of its exposed ends to reduce asymmetric mode conversions.

It is a further object of the invention to provide compensation for variations in individual transducer parameters.

DESCRIPTION OF THE PREFERRED EMBODIMENTS

Figure 1:
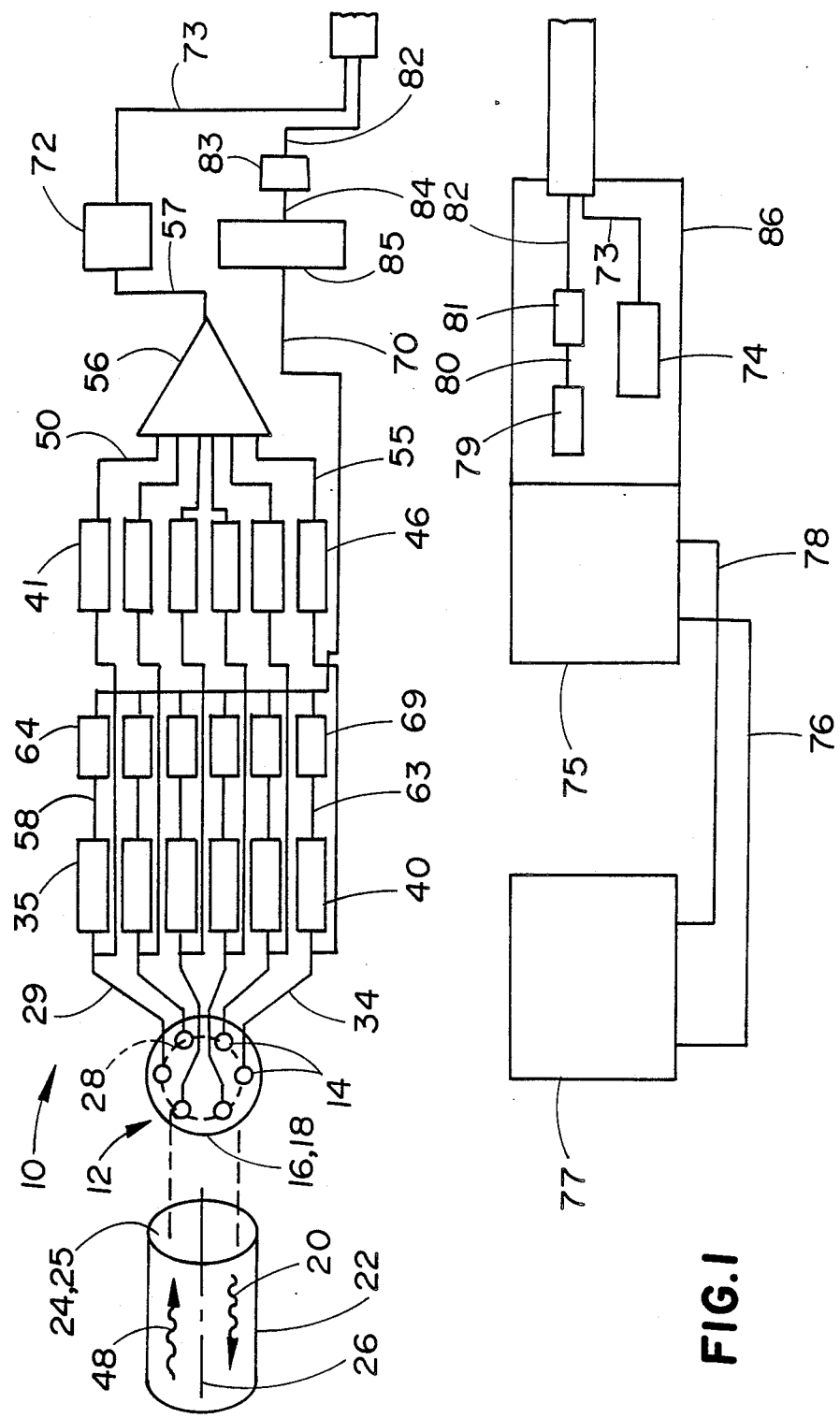
FIG. 1 is one embodiment of the invention.

Referring to FIG. 1, a solid shaft inspection system 10 is shown for detecting physical defects, for example, cracks that arise from metal fatigue. A matrix 12 of transducers 14 are positioned within a predetermined range of one another to form a large transducer head 16 having a large aperture 18 for generating bulk longitudinal acoustic waves 20 into a solid shaft 22. Solid shaft 22 may be, for example, a pump shaft made of stainless steel and having various diameters and threads along its length. FIG. 1 shows end 24 of solid shaft 22 having a surface area 25 transverse to the longitudinal axis 26 of solid shaft 22.

Each transducer 14 includes piezoelectric crystal material. Each transducer 14 may be, for example, 2.54 cm (1 inch) in diameter and arranged in a circle with a diameter of approximately 12.70 cm (5 inches) to form transducer head 16. Transducers 14 may be spaced evenly apart, for example, every sixty degrees on the circle 28.

Figure 2:
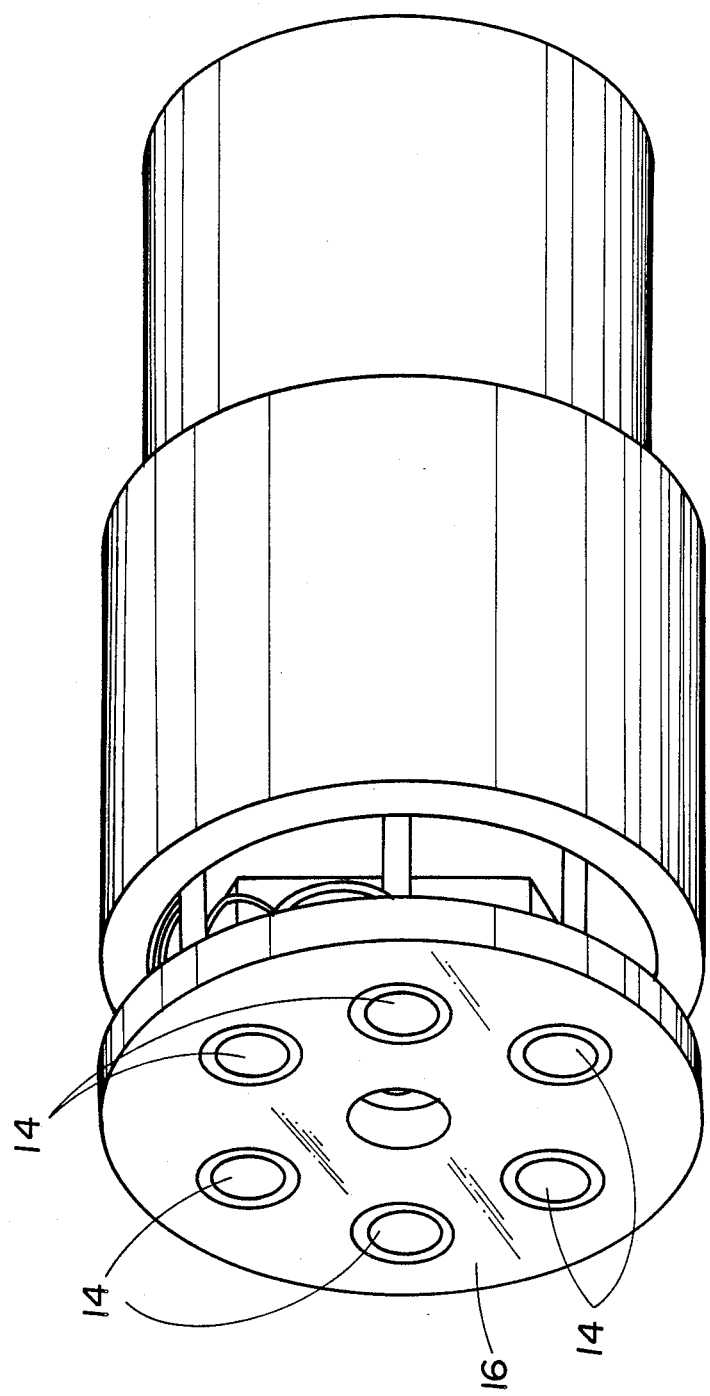
FIG. 2 is a three dimensional view of the transducer head.

FIG. 2 shows a three dimensional view of transducer head 16 with individual tranducers 14 positioned in transducer head 16.

As shown in FIG. 1, each transducer is coupled over a respective lead 29-34 to the output of a respective pulser 35-40. Pulsers 35-40 function to apply a voltage, for example, a negative going 150-volt pulse, for example, a square wave, across a respective transducer 14 for generating bulk longitudinal acoustic waves 20. Each transducer 14 is coupled to a input of a respective preamplifier 41-46 over a respective lead 29-34. Preamplifiers 41-46 function to amplify the electrical signals generated across respective transducers 14 in response to the receipt of reflected ultrasonic waves 48. An output of each preamplifier 41-46 is coupled over respective leads 50-55 to a respective input of summing amplifier 56. Summing amplifier 56 functions to provide the algebraic sum of the input signals on leads 50-55 at the output of summing amplifier 56 on lead 57. The output of summing amplifier 56 provides a single ultrasonic indication which has high amplitude and is not greatly affected by asymmetric mode conversions if transducer head is positioned at the center of the shaft 22 on surface area 25 shown in FIG. 1.

Each pulser 35-40 has an input coupled over respective leads 58-63 to the output of a respective pulse width modulator 64-69. Each pulse width modulator 64-69 has an input coupled to lead 70 which is adapted for receiving a trigger or synchronize pulse. Pulse width modulators 64-69 function to generate a shaped pulse, for example, a square wave of predetermined width with respect to its respective transducer 14 to compensate for variations in transducer parameters.

A unique feature of shaft inspection system 10 is that each transducer 14 in matrix 12 has its own miniaturized pulser 35-40 and preamplifier 41-46 in close proximity, within several centimeters, so that transducer 14 can emit a high-powered ultrasonic or acoustic wave without great loss to the impedence of the piezoelectric crystal material and interconnecting cables. The miniaturized puslers 35-40 and preamplifiers 41-46 were fabricated using components mounted on printed circuit boards using surface mount technology (SMT). Pulsers 35-40 utilized metal oxide semiconductor field effect transistor (MOSFET) technology. Preamplifiers 41-46 provide high gain and low noise amplification.

As shown in FIG. 1, the output of summing amplifier 56 is coupled over lead 57 to an input of analog transmitter 72 which may be, for example, a fiber optic analog transmitter. The output of analog transmitter 72 is coupled over lead or cable 73 to analog receiver 74 which may be an analog fiber optic receiver. The output of analog receiver 74 is coupled to Metrotek model No. MR-106 receiver which functions to amplify and condition the signal which is coupled over lead 76 to oscilloscope 77. The oscilloscope 77 functions to display the analog signal which is an indication of the reflected acoustic waves 48 received by matrix 12.

Receiver 75 also generates a sychronized pulse which is coupled over lead 78 to a oscilloscope 77 and to an input of light emitting diode (LED) driver 79. The output of driver 79 is coupled over lead 80 to an input of digital transmitter 81 which may be, for example, a digital fiber optic transmitter. The output of digital transmitter 81 is coupled over lead or cable 82 to an input of digital receiver 83. Digital receiver 83 may be a fiber optic digital receiver. The output of digital receiver 83 is coupled over lead 84 to buffer 85 which may be, for example, a hex or six-gate buffer. The output of buffer 85 is coupled to lead 70 to pulse width modulators 64-69. Alternatively buffer 85 may include six drivers for driving respective pulse width modulators 64-69 over leads 70a-70f in place of single lead 70.

In operation of the embodiment shown in FIG. 1, a sync pulse from receiver 75 is sent to matrix 12 of transducers 14 via fiber optic cable 82. The sync pulse is then reshaped and split into N signals by a buffer/driver circuit. These signals are applied over lead 70 to the input of pulse-width modulators 64-69, one for each transducer 14 in matrix 12. Each pulse width modulator 64-69 develops a shaped pulse, for example, square wave output. The output pulse width is adjustable in order to compensate for variations in transducer parameters of transducers 14 that affect signal clarity. Output pulses from the pulse width modulators 64-69 are applied to the inputs of high voltage pulsers 35-40. The output of the high voltage pulsers 35-40 is a 150-volt, negative going, square wave that has the same pulse width as the input square wave from respective pulse width modulators 64-69. The high voltage pulsers 35-40 utilizes power MOSFET technology in order to provide the square wave output.

Preamplifier circuits 41-46 consist of a variable gain, low noise, field effect transistor followed by a fixed gain operational amplifier. Each transducer 14 has a respective preamplifier 41-46. The output of preamplifiers 41-46 is fed to the input of summing amplifier 56. The summed output is then coupled over lead 57 to the input of a fiber optic analog transmitter 72 and sent over fiber optic cable 73 to analog receiver 74. Analog receiver 74 and digital transmitter 81 may be part of a communication module which may be, for example, manufactured by Tektronix model No. TM-503 plug-in module.

Both the communication module 86 and the receiver module 75 plug-into a Tektronix TM-503 main frame. Communication module 86 converts the ultrasonic signal from the matrix 12 of transducers 14 back into electrical signals which are supplied to receiver 75 through the rear interface connector of the TM-503 main frame. The output signals of receiver 75 are coupled to the input and external sync channels, respectively of the oscilloscope 77. The oscilloscope 77 is used primarily for observing the received ultrasonic signals. There is no special requirement for the oscilloscope except that it have at least an 80 MHz bandwidth.

An apparatus and method has been described for inspecting a solid shaft for physical defects as small as 0.508 cm (0.200 inches) deep by 3.81 cm (1.5 inches) long comprising a matrix 12 of transducers 14 positioned within a predetermined range of one another to form a large transducer head 16 having a large aperture 18 for generating both longitudinal acoustic waves 20 into a solid shaft 22 from a substantial surface area 25 of the shaft at an exposed end 24, the longitudinal acoustic waves 20 travel in the direction of the longitudinal axis 26 of the solid shaft 22, each transducer 14 may include piezoelectric material, each transducer 14 coupled to the output of a respective pulser 35–40 for applying a voltage across the transducer for generating the bulk longitudinal acoustic waves 20, each transducer 14 coupled to the input of a respective preamplifier 41–46 for amplifying electrical signals from across the transducer in response to the receipt of reflected acoustic waves 48, an output of each preamplifier 41–46 coupled to a respective input 50–55 of a summing amplifier 56 to provide the algebraic sum of the input signals and the output 57 of the summing amplifier 56, each pulser 35–40 having an input coupled to the output of the respective pulse width modulator 64–69, each pulse width modulator 64–69 having an input for receiving a trigger pulse and includes circuitry for generating a square wave of predetermined width with respect to its respective transducer 14 it is driving to compensate for variations in transducer parameters.

What is claimed is:

1. Apparatus for inspecting a solid shaft for physical defects comprising:

a matrix of transducers positioned within a predetermined range of one another to form a transducer head having an aperture for generating bulk longitudinal acoustic waves into a solid shaft from a substantial surface area of the shaft at an exposed end whereby, said longitudinal acoustic waves travel in the direction of the longitudinal axis of the solid shaft, each said transducer coupled to the output of respective pulser for applying a voltage across said transducer for generating bulk longitudinal waves, each said transducer coupled to the input of a respective preamplifier for amplifying electrical signals generated across said transducer in response to the receipt of reflected acoustic waves, an output of each said preamplifier coupled to a respective input of a summing amplifier to provide the algebraic sum of the input signals at an output of the summing amplifier, each said pulser having an input coupled to the output of a respective pulse width modulator, each said pulse width modulator having an input adapted for receiving a trigger pulse and includes circuitry for generating a shaped pulse of predetermined width with respect to its respective transducer it is driving to compensate for variations in transducer parameters.

2. A method for inspecting a solid shaft for physical defects comprising the steps of:

positioning a matrix of transducers within a predetermined range of one another to form a transducer head having an aperture for generating bulk longitudinal acoustic waves into a solid shaft from a substantial surface area of the shaft exposed at one end whereby longitudinal acoustic waves travel in the direction of the longitudinal axis of the solid shaft, coupling each transducer to the output of a respective pulser for applying a voltage across said transducer for generating bulk longitudinal acoustic waves, coupling each said transducer to the input of a respective preamplifier for amplifying electrical signals generated across said transducer in response to the receipt of reflected acoustic waves, coupling an output of each said preamplifier to a respective input of a summing amplifier to provide the algebraic sum of the input signals at an output of the summing amplifiers, coupling the input of each said pulser to the output of a respective pulse width modulator, coupling a trigger pulse to the input of each said pulse width modulator whereby the pulse width modulator generates a shaped pulse of predetermined width with respect to its respective transducer it is driving to compensate for variations in transducer parameters.

* * * * *